(12) United States Patent
Yeo et al.

(10) Patent No.: US 6,324,890 B1
(45) Date of Patent: Dec. 4, 2001

(54) METHOD OF CHARACTERIZING AND SCREENING VOICE COIL MOTOR PIVOT FRICTION IN A LOW VELOCITY REGION

(75) Inventors: Ricky Wei Watt Yeo; KianKeong Ooi; Louis Seng Hong Pang; MingZhong Ding; YangQuan Chen; Beng Wee Quak, all of Singapore (SG)

(73) Assignee: Seagate Technology LLC, Scotts Valley, CA (US)

(*) Notice: Subject to any disclaimer, the term of this patent is extended or adjusted under 35 U.S.C. 154(b) by 0 days.

(21) Appl. No.: 09/584,563

(22) Filed: May 31, 2000

Related U.S. Application Data

(60) Provisional application No. 60/151,695, filed on Aug. 31, 1999.

(51) Int. Cl.[7] ................................................. G01N 33/12
(52) U.S. Cl. ........................................ 73/9; 324/212; 360/75
(58) Field of Search ........................... 324/212; 360/75; 73/9

(56) References Cited

U.S. PATENT DOCUMENTS

| | | | |
|---|---|---|---|
| 5,115,664 | * | 5/1992 | Hegde et al. ................................ 73/9 |
| 5,539,592 | * | 7/1996 | Banks et al. .............................. 360/75 |
| 5,668,690 | * | 9/1997 | Harrison .................................. 360/137 |
| 6,225,799 | * | 5/2001 | Gergel et al. ............................. 324/212 |
| 6,229,664 | * | 5/2001 | Albrecht et al. ........................... 360/75 |

OTHER PUBLICATIONS

Eddy, K., et al., "Bias in Disc Drive Rotary Actuators: Characterization, Prediction, and Compensation", *IEEE Transactions on Magnetics*, 33 (3), pp. 2424–2436, (May 1997).

Wang, F., et al., "Disk Drive Pivot Nonlinearity Modeling Part II: Time Domain", *Proceedings of the American Control Conference*, vol. 3 of 3, Baltimore, MD, pp. 2604–2607, (Jun. 1994).

* cited by examiner

*Primary Examiner*—Daniel S. Larkin
*Assistant Examiner*—Charles Garber
(74) *Attorney, Agent, or Firm*—Schwegman, Lundberg, Woessner & Kluth, P.A.

(57) ABSTRACT

A method of characterizing and screening a disc drive based on a voice coil motor pivot friction developed during a low velocity seek operation consists of determining estimated drive level bias values required by the voice coil motor to move an actuator arm assembly during a fast seek, then determining a low velocity drive level bias values required by the voice coil motor to move an actuator arm assembly during a slow seek, then computing a difference between the estimate drive level bias values and the low velocity drive level bias values, then determining a hit counter value based on comparing the computed difference with a predetermined threshold value, and then characterizing the disc drive based on the hit counter value.

16 Claims, 4 Drawing Sheets

METHOD OF CHARACTERIZING AND SCREENING VOICE COIL MOTOR PIVOT FRICTION IN A LOW VELOCITY REGION

RELATED APPLICATION

This application claims the benefit of U.S. Provisional Application Serial No. 60/151,695, filed Aug. 31, 1999 under 35 U.S.C. 119(e).

FIELD OF THE INVENTION

The present invention relates to the field of mass storage devices. More particularly, this invention relates to a method of characterizing and screening voice coil motor pivot friction in a disc drive.

BACKGROUND OF THE INVENTION

One key component of any computer system is a device to store data. Computer systems have many different places where data can be stored. One common place for storing massive amounts of data in a computer system is on a disc drive. The most basic parts of a disc drive are an information storage disc that is rotated, an actuator that moves a transducer head to various locations over the disc, and electrical circuitry that is used to write and read data to and from the disc. The disc drive also includes circuitry for encoding data so that it can be successfully retrieved and written to the disc surface. A microprocessor controls most of the operations of the disc drive as well as passing the data back to the requesting computer and taking data from a requesting computer for storing to the disc.

The transducer head is typically placed on a small ceramic block, also referred to as a slider, that is aerodynamically designed so that it flies over the disc. The slider is passed over the disc in a transducing relationship with the disc. Most sliders have an air-bearing surface ("ABS") which includes rails and a cavity between the rails. When the disc rotates, air is dragged between the rails and the disc surface causing pressure, which forces the head away from the disc. At the same time, the air rushing past the cavity or depression in the air bearing surface produces a negative pressure area. The negative pressure or suction counteracts the pressure produced at the rails. The slider is also attached to a load spring which produces a force on the slider directed toward the disc surface. The various forces equilibrate so the slider flies over the surface of the disc at a particular desired fly height. The fly height is the distance between the disc surface and the transducing head, which is typically the thickness of the air lubrication film. This film eliminates the friction and resulting wear that would occur if the transducing head and disc were in mechanical contact during disc rotation. In some disc drives, the slider passes through a layer of lubricant rather than flying over the surface of the disc.

Information representative of data is stored on the surface of the storage disc. Disc drive systems read and write information stored on tracks on storage discs. Transducers, in the form of read/write heads attached to the sliders, located on both sides of the storage disc, read and write information on the storage discs when the transducers are accurately positioned over one of the designated tracks on the surface of the storage disc. The transducer is also said to be moved to a target track. As the storage disc spins and the read/write head is accurately positioned above a target track, the read/write head can store data onto a track by writing information representative of data onto the storage disc. Similarly, reading data on a storage disc is accomplished by positioning the read/write head above a target track and reading the stored material on the storage disc. To write on or read from different tracks, the read/write head is moved radially across the tracks to a selected target track. The data is divided or grouped together on the tracks. In some disc drives, the tracks are a multiplicity of concentric circular tracks. In other disc drives, a continuous spiral is one track on one side of disc drive. Servo feedback information is used to accurately locate the transducer head. The actuator assembly is moved to the required position and held very accurately during a read or write operation using the servo information.

The actuator is rotatably attached to a shaft via a bearing cartridge which generally includes one or more sets of ball bearings. The shaft is attached to the base and may be attached to the top cover of the disc drive. A yoke is attached to the actuator. The voice coil is attached to the yoke at one end of the rotary actuator. The voice coil is part of a voice coil motor which is used to rotate the actuator and the attached transducer or transducers. A permanent magnet is attached to the base and cover of the disc drive. The voice coil motor which drives the rotary actuator comprises the voice coil and the permanent magnet. The voice coil is attached to the rotary actuator and the permanent magnet is fixed on the base. A yoke is generally used to attach the permanent magnet to the base and to direct the flux of the permanent magnet. Since the voice coil sandwiched between the magnet and yoke assembly is subjected to magnetic fields, electricity can be applied to the voice coil to drive it so as to position the transducers at a target track.

The voice coil motor pivot friction has an increasing impact on hard disc drive servo control. This is generally true in cases where the voice coil motor uses a ball bearing design, and where the hard disc drive has high tracks per inch. In the case of high tracks per inch, the width of a track is so minute, that the movement of the bearing may also become minuscule, and that the friction at these low velocities can become significantly dominant. This friction dominance at low velocity displacement due to high tracks per inch has become extremely important in low cost desk top hard disc drive servo controller design. This friction at low velocities introduces a nonlinear dynamics on the hard disc drive servo controller. It is generally easier to design disc drive controllers for linear systems. Small nonlinearities can often be neglected in the design of controllers, or even approximated by linearizations. It is generally difficult to include the nonlinear dynamics introduced by the voice coil motor pivot friction in the design of the disc drive controllers. In general at high velocities the voice coil motor friction can be characterized as linear, but at low velocities the voice coil motor pivot friction cannot be linearized. If a linear design is used for the controller at low velocities when the voice coil pivot friction is present, bias estimator in the controller can estimate abnormally high bias values, which can result in unexpected behavior of the hard disc drive during a seek operation, such as sample errors resulting in seek failures, and the inability of the voice coil motor to park against the latch as the bias estimator may have diverged to a point where the bias force may be equivalent to the parking current in the opposite direction.

The voice coil motor pivot friction can vary significantly with large variations in the manufacturing tolerances in the hard disc drive components. Currently there are no reliable, accurate and cost effective methods to characterize the voice coil pivot friction.

What is needed is a reliable, accurate, and cost effective method of characterizing and salvaging disc drives having acceptable voice coil motor pivot friction levels.

SUMMARY OF THE INVENTION

A disc drive includes a base and a disc rotatably attached to the base. The disc drive also includes an actuator arm assembly rotatably attached to said base and a voice coil motor for moving the actuator arm assembly. The actuator arm assembly includes a transducer head in a transducing relationship with respect to the disc. The disc drive further includes a disc drive controller for controlling the movement of the actuator arm assembly during track follow and track seek operations. The disc drive controller includes a servo controller coupled to the voice coil motor and the actuator arm assembly for running a slow seek to ascertain a low velocity drive level friction bias values required by the voice coil motor to move the actuator arm assembly to a predetermined number of zones on the disc drive. Further the servo controller runs a fast seek to determined estimated drive level bias values required by the voice coil motor to move the actuator arm assembly to the predetermined number of zones. The disc drive controller further includes an analyzer coupled to the servo controller for computing a difference between the drive level friction values and the estimated drive level bias values for the predetermined number of zones. The disc drive controller further includes a comparator coupled to the analyzer to compare the computed difference with a predetermined threshold value. A hit counter coupled to the comparator monitors a hit counter value based on the outcome of the comparison for the predetermined number of zones, and characterizes the disc drive based on the hit counter value.

Also discussed is a method of characterizing the voice coil motor pivot friction during a low velocity operation of the disc drive. The method comprises determining estimated drive level bias values required by the voice coil motor to move an actuator arm assembly during a fast seek to a predetermined number of zones, and then determining a low velocity drive level friction bias values required by the voice coil motor to move an actuator arm assembly during a slow seek to the predetermined number of zones. Then computing differences between the low velocity drive level friction bias values and the estimated drive level bias values for the predetermined number of zones. Then the computed differences are compared to a predetermined threshold value to determined a hit counter value. Then the disc drive is characterized based on the hit counter value.

Advantageously, the procedure set forth above and the apparatus for implementing the characterizing of the voice coil motor pivot friction is reliable, accurate, and a cost effective method for characterizing and salvaging disc drives having acceptable voice coil motor pivot friction levels. The above procedure can be incorporated in microcode and used to control the servo circuitry to implement the invention.

DESCRIPTION OF THE PREFERRED EMBODIMENT

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
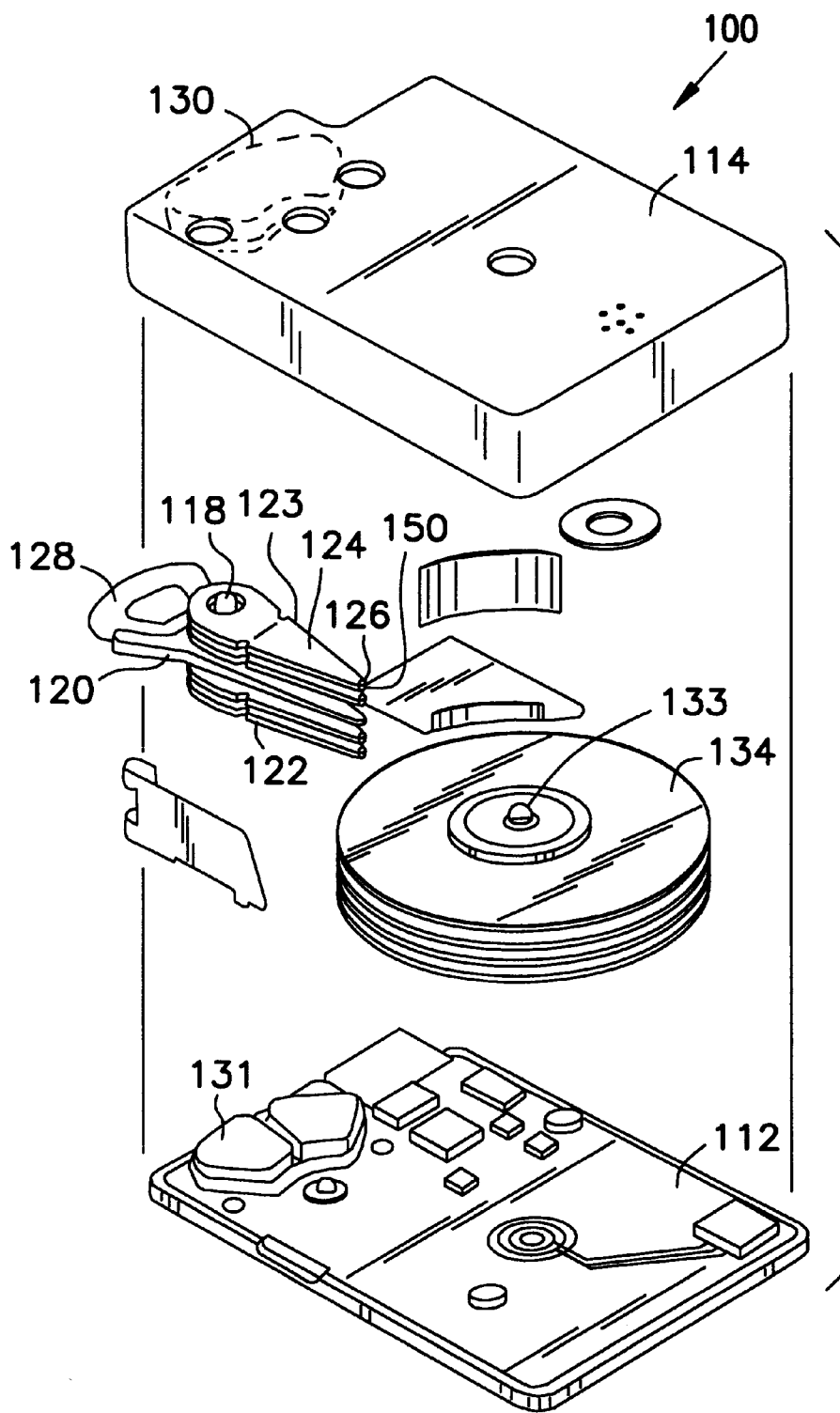
FIG. 1 is an exploded view of a disc drive with a multiple disc stack.

The invention described in this application is useful with all mechanical configurations of disc drives having either rotary or linear actuation. In addition, the invention is also useful in all types of disc drives including hard disc drives, zip drives, floppy disc drives and any other type of drives where unloading the transducer from a surface and parking the transducer may be desirable. FIG. 1 is an exploded view of one type of a disc drive 100 having a rotary actuator. The disc drive 100 includes a housing or base 112, and a cover 114. The base 112 and cover 114 form a disc enclosure. An inertia ring 500 is attached to the cover 114. Rotatably attached to the base 112 on an actuator shaft 118 is an actuator arm assembly 120. The actuator arm assembly 120 includes a comb-like structure 122 having a plurality of actuator arms 123. Attached to the separate actuator arms 123 on the comb 122, are load beams or load springs 124. Load beams or load springs are also referred to as suspensions. Attached at the end of each load spring 124 is a slider 126 which carries a magnetic transducer 150. The slider 126 with the transducer 150 form what is many times called the head. It should be noted that many sliders have one transducer 150 and that is what is shown in the figures. It should also be noted that this invention is equally applicable to sliders having more than one transducer, such as what is referred to as an MR or magneto resistive head in which one transducer 150 is generally used for reading and another is generally used for writing. On the end of the actuator arm assembly 120 opposite the load springs 124 and the sliders 126 is a voice coil 128.

Attached within the base 112 is a first magnet 131 and a second magnet 130. As shown in FIG. 1, the second magnet 130 is associated with the cover 114. The first and second magnets 130, 131, and the voice coil 128 are the key components of a voice coil motor which applies a force to the actuator assembly 120 to rotate it about the actuator shaft 118. Also mounted to the base 112 is a spindle motor. The spindle motor includes a rotating portion called the spindle hub 133. In this particular disc drive, the spindle motor is within the hub. In FIG. 1, a number of discs 134 are attached to the spindle hub 133. In other disc drives a single disc or a different number of discs may be attached to the hub. The invention described herein is equally applicable to disc drives which have a plurality of discs as well as disc drives that have a single disc. The invention described herein is also equally applicable to disc drives with spindle motors which are within the hub 133 or under the hub.

Figure 2:
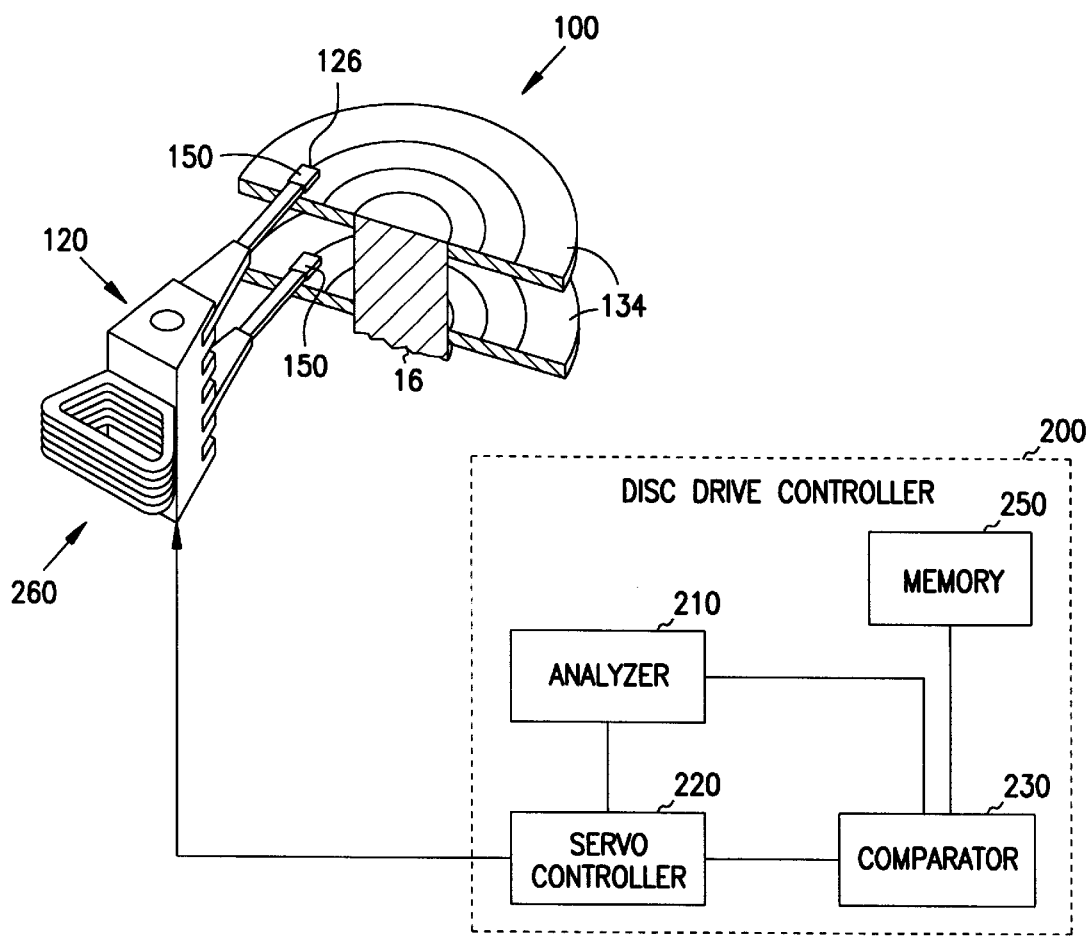
FIG. 2 is a schematic representation of a disc drive including portions of the disc drive controller used in characterizing and screening the voice coil motor pivot friction.

FIG. 2 is a schematic representation of a disc drive 100 and further includes selected portions of a disc drive controller 200 used in characterizing the voice coil motor pivot friction of the disc drive 100. As shown in FIG. 2, the disc drive 100 includes at least one disc 134 rotatably attached to a base (not shown) through a shaft 16. The disc drive 100 also includes an actuator arm assembly 120 having a transducer head 126 and a transducer 150 for reading from the disc 134 and writing to the disc 134. The actuator arm assembly 120 carrying the transducer 126 in a transducing relation with respect to the disc 134. The actuator assembly 120 is attached to a voice coil motor 260 (not all parts of the voice coil motor are shown for clarity) to move the actuator arm assembly 120 during a seek operation. A disc drive controller 200 is coupled to the voice coil motor 260. The disc drive controller 200 includes a servo controller 220 to run a fast and slow seeks and to ascertain drive level friction bias values and low velocity drive level friction bias values required by the voice coil motor to move the actuator arm assembly during the fast and slow seeks to a predetermined number of zones. The disc drive controller 200 also includes an analyzer 210, coupled to the servo controller 220, to compute a difference between the ascertained drive level friction values and the estimated drive level bias values, respectively for the predetermined number of zones. The disc drive controller 220 further includes a comparator 230, coupled to the servo controller 220, to compare the computed difference between the low velocity drive level friction values and the estimated drive level bias values with a predetermined threshold value. In one embodiment the disc drive controller 200 comprises a hit counter 240 coupled to the comparator 230 to monitor a hit counter value based on the outcome of the comparison for the predetermined number of zones. Also in this embodiment the disc drive controller 200 rejects the disc drive 100 when the hit counter value exceeds a predetermined number. In another embodiment the disc drive controller 200 includes a memory 250 coupled to the hit counter 240 and the comparator 230 to store the ascertained low velocity drive level bias values, estimated drive level bias values and the hit counter value. In another embodiment the comparator 230 computes an absolute difference between the drive level friction values and the estimated drive level bias values for the predetermined number of zones.

Figure 3:
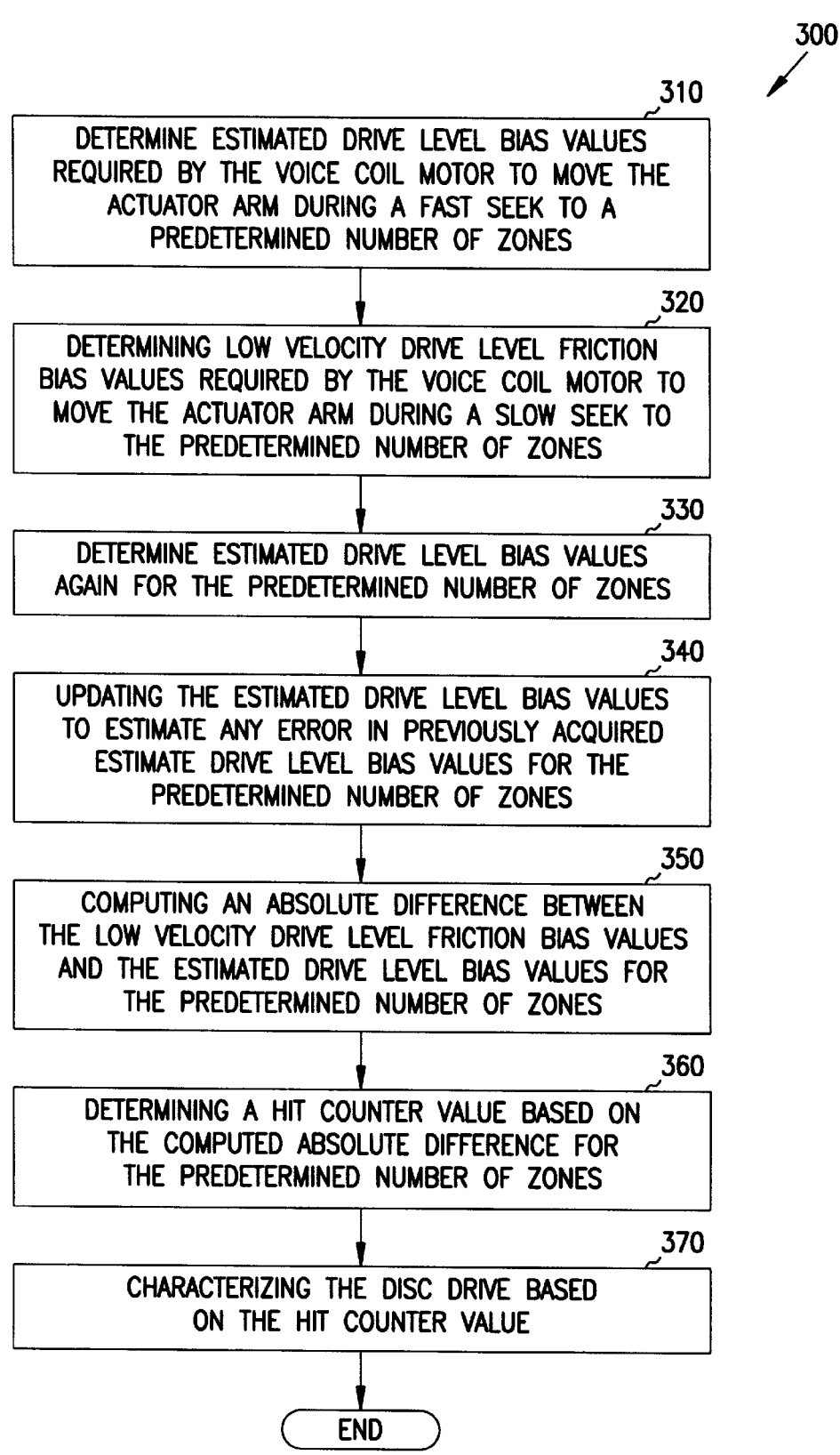
FIG. 3 is a flow diagram of the procedure of the instant invention.

FIG. 3 is a flow diagram of the method of characterizing and screening a voice coil motor pivot friction during a low velocity operation of a disc drive 100. The first step in the method of characterizing and screening the disc drive 100 is to determine estimated drive level bias values 310 required by the voice coil motor to move an actuator arm assembly 120 during a fast seek to a predetermined number of zones on the disc drive 100. Then to determine low velocity drive level friction bias values 320 required by the voice coil motor to move the actuator arm assembly during a slow seek to the predetermined number of zones. In one embodiment the next step in the method is to determine again the estimated drive level bias values during a fast seek 330, and to update the estimated drive level bias values to eliminate any errors that might have occurred in any previously acquired estimated drive level bias values for the predetermined number of zones 340. Then to compute a difference between the low velocity drive level friction bias values and the estimated drive level bias values 350, respectively for the predetermined number of zones. In one embodiment, the computing step involves in computing an absolute difference between the low velocity drive level friction bias values and the estimated drive level bias values, respectively for the predetermined number of zones 350. Then the next step is to determine a hit counter value based on comparing the computed absolute difference with a predetermined threshold value for the predetermined number of zones 360. In one embodiment the hit counter value is determined based on a number of times the computed absolute difference exceeds the predetermined threshold value for the predetermined number of zones. Then the last step in the method is to characterize the disc drive 100 based on the hit counter value 370. In one embodiment the disc drive 100 is characterized based on comparing the hit counter value to a predetermined number. In another embodiment the disc drive 100 is rejected, if the hit counter value exceeds the predetermined number, and the disc drive 100 is accepted, if the hit counter value does not exceed the predetermined number.

In one embodiment the step of determining estimated drive level bias values includes running a drive level bias calibration using a fast seek to ascertain estimated drive level bias values required by the voice coil motor to move the actuator arm assembly 120 to the predetermined number of zones on the disc drive 100, and further includes monitoring the estimated drive level bias values for the predetermined number of zones on the disc drive during the drive level bias calibration.

In another embodiment the step of determining low velocity drive level bias values includes running a slow seek to ascertain the low velocity drive level friction bias values required by the voice coil motor to move the actuator arm assembly 120 to the predetermined number of zones on the disc drive 10, and the step of determining low velocity further includes monitoring the low velocity drive level friction bias values during the slow seek for the predetermined number of zones on the disc drive 100.

In one embodiment the step of computing further includes running the drive level bias calibration again using the fast seek to ascertain the estimated drive level bias values for the voice coil motor to move the actuator arm assembly 120 to the predetermined number of zones on the disc drive 100. Then to monitor the estimated drive level bias values again for the predetermined number of zones on the disc drive 100. Then to update the estimated drive level bias values again to eliminate any errors that might have occurred in the previously acquired drive bias values for the predetermined number of zones. Then to compute a difference between the low velocity drive level friction bias values and the estimated drive level bias values for the predetermined number of zones.

In one embodiment the steps of running the slow seek and monitoring the low velocity drive level bias values further includes running the slow seek on a track of a zone to ascertain and monitor the low velocity drive level friction bias values for the voice coil motor to move the actuator arm assembly 120 to a first predetermined track position and for staying on the first predetermined track position for a predetermined amount of time, then to run a slow seek again to ascertain and monitor the low velocity drive level friction bias values for the voice coil motor to move the actuator arm assembly 120 to a second predetermined track position and for staying on the second predetermined track position for the predetermined amount of time, and then to again run a slow seek to ascertain and monitor the low velocity drive level friction bias values for the voice coil motor to move the actuator arm assembly 120 to a third predetermined track position and for staying on the third predetermined track position for the predetermined amount of time. The above steps are repeated for a predetermined number of tracks on the zone, and for the predetermined number of zones to ascertain and monitor the low velocity drive level friction bias values.

Figure 4:
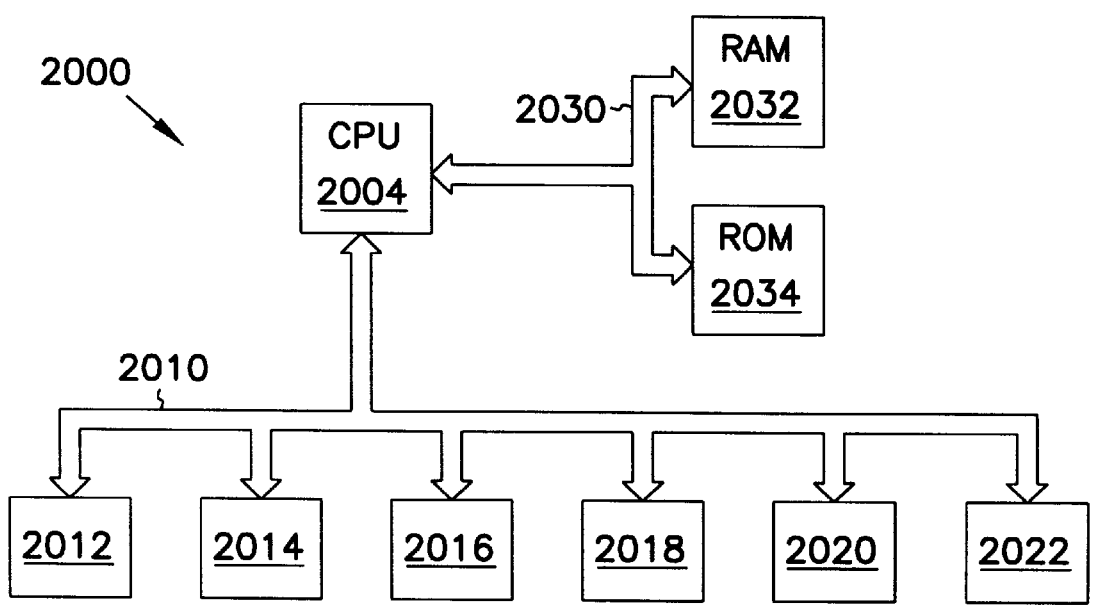
FIG. 4 is a schematic view of a computer system.

In one embodiment the predetermined amount of time is approximately in the range of about 11 milliseconds to 330 milliseconds, the predetermined number is approximately in the range of about 1 to 5, the predetermined number of tracks is approximately in the range of about 50 to 200, and the predetermined number of zones on the disc drive is approximately in the range of about 5 to 10. In another embodiment the first predetermined track position is around a center of a track, the second predetermined track position is offset about 25% of the track from the center of the track, and the third predetermined track position is offset about 50% of the track from the center of the track FIG. 4 is a schematic view of a computer system. Advantageously, the invention is well-suited for use in a computer system 2000. The computer system 2000 may also be called an electronic system or an information handling system and includes a central processing unit, a memory and a system bus. The information handling system includes a central processing unit 2004, a random access memory 2032, and a system bus 2030 for communicatively coupling the central processing unit 2004 and the random access memory 2032. The information handling system 2000 includes a disc drive device which includes the ramp described above. The information handling system 2002 may also include an input/output bus 2010 and several devices peripheral devices, such as 2012, 2014, 2016, 2018, 2020, and 2022 may be attached to the input output bus 2010. Peripheral devices may include hard disc drives, magneto optical drives, floppy disc drives, monitors, keyboards and other such peripherals. Any type of disc drive may use the method for loading or unloading the slider onto the disc surface as described above.

CONCLUSION

In conclusion, a disc drive controller 200 characterizes the voice coil motor pivot friction during a low velocity operation of the disc drive. The method comprises determining estimated drive level bias values required by the voice coil motor to move an actuator arm assembly during a fast seek to a predetermined number of zones 310, and then determining a low velocity drive level friction bias values required by the voice coil motor to move an actuator arm assembly during a slow seek to the predetermined number of zones 320. Then computing differences between the low velocity drive level friction bias values and the estimated drive level bias values for the predetermined number of zones 350. Then comparing the computed differences to a predetermined threshold value to determined a hit counter value 360. Then characterizing the disc drive based on the hit counter value 370.

Also discussed is a disc drive 100 including an actuator arm assembly 120 having a transducer head 126 and a transducer 150 for reading and writing to the disc 134. The actuator arm assembly 120 carrying the transducer 126 in a transducing relation with respect to the disc 134. The actuator assembly 120 is attached to a voice coil motor 260 (not all parts of the voice coil motor are shown for clarity) to move the actuator arm assembly 120 during a seek operation. A disc drive controller 200 is coupled to the voice coil motor 260, includes a servo controller 220 to run a fast and slow seeks and to ascertain drive level friction bias values and low velocity drive level friction bias values required by the voice coil motor to move the actuator arm assembly for a predetermined number of zones during the fast and slow seeks. The disc drive controller 200 also includes an analyzer 210, coupled to the servo controller 220, to compute a difference between the drive level friction values and the estimated drive level bias values, respectively for the predetermined number of zones. The disc drive controller 220 further includes a comparator 230, coupled to the servo controller 220, to compare the computed difference between the low velocity drive level friction values and the estimated drive level bias values with a predetermined threshold value. In one embodiment the disc drive controller 200 comprises a hit counter 240 coupled to the comparator 230 to monitor a hit counter value based on the outcome of the comparison for the predetermined number of zones. Also in this embodiment the disc drive controller 200 rejects the disc drive 100 when the hit counter value exceeds the predetermined number. In another embodiment the disc drive controller 200 includes a memory 250 coupled to the hit counter 240 and the comparator 230 to store the low velocity drive level bias values, estimated drive level bias values and the hit counter value. In another embodiment the comparator 230 computes an absolute difference between the drive level friction values and the estimated drive level bias values for the predetermined number of zones.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method of characterizing and screening a disc drive based on a voice coil motor pivot friction developed during a low velocity seek operation, comprising steps of:

(a) determining estimated drive level bias values required by the voice coil motor to move an actuator arm assembly during a fast seek to a predetermined number of zones;

(b) determining low velocity drive level friction bias values required by the voice coil motor to move the actuator arm assembly during a slow seek to the predetermined number of zones;

(c) computing a difference between the low velocity drive level friction bias values and the estimated drive level bias values, respectively for the predetermined number of zones;

(d) determining a hit counter value based on comparing the computed difference with a predetermined threshold value for the predetermined number of zones; and (e) characterizing the disc drive based on the hit counter value.

2. The method of claim 1, wherein the characterizing step (e) comprises (e)(i) rejecting the disc drive, if the hit counter value exceeds a predetermined number.

3. The method of claim 1, wherein the determining estimated drive level bias values step (a) further comprising steps of:

(a)(i) running a drive level bias calibration using a fast seek to ascertain the estimated drive level bias values required by the voice coil motor to move the actuator arm assembly to the predetermined number of zones on the disc drive; and (a)(ii) monitoring the estimated drive level bias values for the predetermined number of zones on the disc drive during the drive level bias calibration.

4. The method of claim 3, wherein the determining low velocity drive level bias values step (b) further comprising steps of:

(b)(i) running a slow seek to ascertain the low velocity drive level friction bias values required by the voice coil motor to move the actuator arm assembly to the predetermined number of zones on the disc drive; and (b)(ii) monitoring the low velocity drive level friction bias values during the slow seek for the predetermined number of zones on the disc drive.

5. The method of claim 4, wherein the step of computing (c) further comprising steps of:

(c)(i) running the drive level bias calibration again using the fast seek to ascertain the estimated drive level bias values for the voice coil motor to move the actuator arm assembly to the predetermined number of zones on the disc drive;

(c)(ii) monitoring the estimated drive level bias values again for the predetermined number of zones on the disc drive;

(c)(iii) updating the estimated drive level bias values to eliminate any error in previously acquired estimated drive level bias values; and (c)(iv) computing a difference between the low velocity drive level friction bias values and the estimated drive level bias values for the predetermined number of zones.

6. The method of claim 5, wherein the computing step (c) comprises (c)(v) computing an absolute difference between drive level friction values and the estimated drive level bias values, respectively.

7. The method of claim 6, wherein the determining the hit counter value step (d) further comprising the steps of:

(d)(i) comparing the computed difference in the drive level friction bias values and the estimated drive level bias values, respectively with a predetermined threshold value;

(d)(ii) monitoring number of times the computed difference exceeds the predetermined threshold value for the predetermined number of zones based on the outcome of the comparison; and (d)(iii) updating a hit counter value by the number of times the computed difference exceeds the predetermined threshold value for the predetermined number of zones.

8. The method of claim 7, wherein the step of running the slow seek (b)(i) and step of monitoring the low velocity drive level friction bias values (b)(ii) further comprising:

(b)(i)(i) running the slow seek on a track of a zone to ascertain the low velocity drive level friction bias values for the voice coil motor to move the actuator arm assembly to a first predetermined track position and for staying on the first predetermined track position for a predetermined amount of time;

(b)(ii)(i) monitoring the low velocity drive level friction bias values during the slow seek to the first predetermined track position;

(b)(i)(ii) running a slow seek on a second predetermined track position of the track of the zone to ascertain the low velocity drive level friction bias values for the voice coil motor to move the actuator arm assembly to the second predetermined track position and for staying on the second predetermined track position for the predetermined amount of time;

(b)(ii)(ii) monitoring the low velocity drive level friction bias values during the slow seek to the second predetermined track position;

(b)(i)(iii) running a slow seek on a third predetermined track position the track of the zone to ascertain the low velocity drive level friction bias values for the voice coil motor to move the actuator arm assembly to the third predetermined track position and for staying on the third predetermined track position for the predetermined amount of time;

(b)(ii)(iii) monitoring the low velocity drive level friction bias values during the slow seek to the third predetermined track position;

(b)(iii) repeating the above steps for a predetermined number of tracks on the zone; and (b)(iv) repeating the above steps again for the predetermined number of zones.

9. The method of claim 8, wherein the monitoring the low velocity drive level friction bias values further comprising storing the monitored low velocity drive level friction bias values, the monitored estimated drive level bias values, the hit counter value, and the predetermined threshold value.

10. The method of claim 9, wherein the predetermined amount of time is approximately in the range of about 11 milliseconds to 330 milliseconds, wherein the predetermined number is approximately in the range of about 1 to 5, wherein the predetermined number of tracks on a zone is approximately in the range of about 50 to 200, and wherein the predetermined number of zones on the disc drive is approximately in the range of about 5 to 10.

11. The method of claim 10, wherein the first predetermined track position is at a center of a track, wherein the second predetermined track position is offset by about 25% of the track from the center of the track, and wherein the third predetermined track position is offset by about 50% of the track from the center of the track.

12. A disc drive, comprising:

a base;

a disc rotatably attached to the base;

an actuator arm assembly for carrying a transducer head in a transducing relation with respect to the disc;

a voice coil motor to move the actuator arm assembly;

a disc drive controller, coupled to the voice coil motor further includes:

a servo controller, coupled to the voice coil motor and the actuator arm assembly, wherein the servo controller runs a slow seek to ascertain a low velocity drive level friction bias values required by the voice coil motor to move the actuator arm assembly for a predetermined number of zones on the disc drive, wherein the servo controller further runs a fast seek to determine estimated drive level bias values required by the voice coil motor to move the actuator arm assembly for the predetermined number of zones;

an analyzer, coupled to the servo controller, computes a difference between the drive level friction values and the estimated drive level bias values for the predetermined number of zones;

a comparator, coupled to the analyzer, compares the computed difference between the low velocity drive level friction values and the estimated drive level bias values with a predetermined threshold value; and a hit counter, coupled to the comparator, wherein the hit counter monitors a hit counter value based on the outcome of the comparison for the predetermined number of zones, and wherein the analyzer rejects the disc drive when the hit counter value exceeds a predetermined number.

13. The disc drive of claim 12, wherein the servo controller further runs the slow seek to ascertain the low velocity drive level bias values required by the voice coil motor to move the actuator arm assembly to a predetermined number of tracks on the zone of the predetermined number of zones.

14. The disc drive of claim 12, further includes a memory coupled to the counter and the comparator to store the low velocity drive level friction bias values, the estimated drive level bias values, the hit counter value, and the predetermined threshold value.

15. The disc drive of claim 14, wherein the servo controller further monitors the low velocity drive level bias values required by the voice coil motor to move the actuator arm assembly to a first, second and third track positions on the track for the predetermined number of tracks during the slow seek.

16. The disc drive of claim 12, wherein the analyzer computes an absolute difference between the drive level friction values and the estimated drive level bias values.

* * * * *